United States Patent
Rao et al.

(10) Patent No.: US 7,711,404 B2
(45) Date of Patent: May 4, 2010

(54) PATIENT DATA MINING FOR LUNG CANCER SCREENING

(75) Inventors: R. Bharat Rao, Berwyn, PA (US); Sathyakama Sandilya, Cranbury, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 807 days.

(21) Appl. No.: 10/287,073

(22) Filed: Nov. 4, 2002

(65) Prior Publication Data

US 2003/0120133 A1    Jun. 26, 2003

Related U.S. Application Data

(60) Provisional application No. 60/335,542, filed on Nov. 2, 2001.

(51) Int. Cl.
*A61B 5/05* (2006.01)
(52) U.S. Cl. .................. 600/407; 600/410; 435/6; 435/325; 536/23.1; 705/3
(58) Field of Classification Search .............. 435/6, 435/325; 536/23.1; 705/3; 600/407, 410
See application file for complete search history.

(56) References Cited

U.S. PATENT DOCUMENTS

| | | |
|---|---|---|
| 4,946,679 A | 8/1990 | Thys-Jacobs |
| 5,307,262 A | 4/1994 | Ertel |
| 5,359,509 A | 10/1994 | Little et al. |
| 5,365,425 A | 11/1994 | Torma et al. |
| 5,508,912 A | 4/1996 | Schneiderman |

(Continued)

FOREIGN PATENT DOCUMENTS

DE    198 20 276    11/1999

(Continued)

OTHER PUBLICATIONS

Evans S et al: "Using data mining to characterize DNA mutations by patient clinical features" 1997 AMIA Annual Fall Symposium. A Informatics Association. Proceeedings, Proceedings of 1997 AMIA Annual Fall Symposium the Emergence of Internetable Health Care Systems That Really Work, Nashville, TN, USA, 25-29 0, pp. 253-257, XP002270751 1997, Philadelphia, PA, USA, Hanley & Belfus, USA abstract Section: Methods.

(Continued)

*Primary Examiner*—Brian Casler
*Assistant Examiner*—John F Ramirez
(74) *Attorney, Agent, or Firm*—Joshua Ryan

(57) ABSTRACT

A system and method for lung cancer screening is provided. The system includes a database including structured patient information for a patient population and a domain knowledge base including information about lung cancer; an individual patient record; and a processor for analyzing the patient record with data from the database to determine if a patient has indications of lung cancer. The method includes the steps of inputting patient-specific data into a patient record; performing at least one lung cancer screening procedure on a patient, wherein at least one result from the at least one procedure is inputted into the patient record in a structured format; and analyzing the patient record with a domain knowledge base to determine if the patient has indications of lung cancer.

19 Claims, 3 Drawing Sheets

U.S. PATENT DOCUMENTS

| | | | |
|---|---|---|---|
| 5,544,044 A | | 8/1996 | Leatherman |
| 5,557,514 A | | 9/1996 | Seare et al. |
| 5,619,991 A | | 4/1997 | Sloane |
| 5,652,842 A | | 7/1997 | Siegrist, Jr. et al. |
| 5,657,255 A | | 8/1997 | Fink et al. |
| 5,664,109 A | * | 9/1997 | Johnson et al. ............... 705/2 |
| 5,669,877 A | | 9/1997 | Blomquist |
| 5,706,441 A | | 1/1998 | Lockwood |
| 5,724,379 A | | 3/1998 | Perkins et al. |
| 5,724,573 A | | 3/1998 | Agrawal et al. |
| 5,737,539 A | | 4/1998 | Edelson et al. |
| 5,738,102 A | | 4/1998 | Lemelson |
| 5,811,437 A | | 9/1998 | Singh et al. |
| 5,832,450 A | | 11/1998 | Myers et al. |
| 5,835,897 A | | 11/1998 | Dang |
| 5,845,253 A | | 12/1998 | Rensimer et al. |
| 5,899,998 A | | 5/1999 | McGauley et al. |
| 5,903,889 A | | 5/1999 | de la Huerga et al. |
| 5,908,383 A | | 6/1999 | Brynjestad |
| 5,924,073 A | | 7/1999 | Tyuluman et al. |
| 5,924,074 A | | 7/1999 | Evans |
| 5,935,060 A | | 8/1999 | Iliff |
| 5,939,528 A | * | 8/1999 | Clardy et al. ............... 530/350 |
| 6,039,688 A | | 3/2000 | Douglas et al. |
| 6,067,466 A | | 5/2000 | Selker et al. |
| 6,078,894 A | | 6/2000 | Clawson et al. |
| 6,081,786 A | * | 6/2000 | Barry et al. .................... 705/3 |
| 6,083,693 A | | 7/2000 | Nandabalan et al. |
| 6,108,635 A | | 8/2000 | Herren et al. |
| 6,125,194 A | * | 9/2000 | Yeh et al. .................... 382/132 |
| 6,128,620 A | | 10/2000 | Pissanos et al. |
| 6,139,494 A | | 10/2000 | Cairnes |
| 6,151,581 A | * | 11/2000 | Kraftson et al. ............... 705/3 |
| 6,173,280 B1 | | 1/2001 | Ramkumar et al. |
| 6,196,970 B1 | | 3/2001 | Brown |
| 6,212,526 B1 | | 4/2001 | Chaudhuri et al. |
| 6,253,186 B1 | | 6/2001 | Pendleton, Jr. |
| 6,259,890 B1 | | 7/2001 | Driscoll et al. |
| 6,266,645 B1 | | 7/2001 | Simpson |
| 6,272,472 B1 | | 8/2001 | Danneels et al. |
| 6,322,502 B1 | | 11/2001 | Schoenberg et al. |
| 6,322,504 B1 | | 11/2001 | Kirshner |
| 6,338,042 B1 | | 1/2002 | Paizis |
| 6,381,576 B1 | * | 4/2002 | Gilbert ........................... 705/2 |
| 6,468,210 B1 | | 10/2002 | Iliff |
| 6,478,737 B2 | | 11/2002 | Bardy |
| 6,484,144 B2 | | 11/2002 | Martin et al. |
| 6,529,876 B1 | | 3/2003 | Dart et al. |
| 6,551,243 B2 | | 4/2003 | Bocionek et al. |
| 6,551,266 B1 | | 4/2003 | Davis, Jr. |
| 6,611,825 B1 | | 8/2003 | Billheimer et al. |
| 6,611,846 B1 | | 8/2003 | Stoodley |
| 6,641,532 B2 | | 11/2003 | Iliff |
| 6,645,959 B1 | | 11/2003 | Bakker-Arkema et al. |
| 6,678,669 B2 | | 1/2004 | Lapointe et al. |
| 6,754,655 B1 | | 6/2004 | Segal |
| 6,802,810 B2 | | 10/2004 | Ciamiello et al. |
| 6,804,656 B1 | * | 10/2004 | Rosenfeld et al. ............... 705/3 |
| 6,826,536 B1 | | 11/2004 | Forman |
| 6,839,678 B1 | | 1/2005 | Schmidt et al. |
| 6,903,194 B1 | | 6/2005 | Sato et al. |
| 6,915,254 B1 | | 7/2005 | Heinze et al. |
| 6,915,266 B1 | | 7/2005 | Saeed et al. |
| 6,941,271 B1 | | 9/2005 | Soong |
| 6,961,687 B1 | | 11/2005 | Myers, Jr. et al. |
| 6,988,075 B1 | | 1/2006 | Hacker |
| 7,058,658 B2 | | 6/2006 | Mentzer |
| 7,130,457 B2 | * | 10/2006 | Kaufman et al. ............ 382/128 |
| 7,307,543 B2 | | 12/2007 | Rosenfeld et al. |
| 2001/0011243 A1 | | 8/2001 | Dembo et al. |
| 2001/0023419 A1 | * | 9/2001 | Lapointe et al. ............... 706/15 |
| 2001/0032195 A1 | | 10/2001 | Graichen et al. |
| 2001/0041991 A1 | | 11/2001 | Segal et al. |
| 2001/0051882 A1 | | 12/2001 | Murphy et al. |
| 2002/0002474 A1 | | 1/2002 | Michelson et al. |
| 2002/0010597 A1 | | 1/2002 | Mayer et al. |
| 2002/0026322 A1 | | 2/2002 | Snowden et al. |
| 2002/0026332 A1 | | 2/2002 | Snowden et al. |
| 2002/0032581 A1 | | 3/2002 | Reitberg |
| 2002/0035316 A1 | | 3/2002 | Drazen |
| 2002/0077853 A1 | | 6/2002 | Boru et al. |
| 2002/0082480 A1 | | 6/2002 | Riff et al. |
| 2002/0087361 A1 | | 7/2002 | Benigno et al. |
| 2002/0099570 A1 | | 7/2002 | Knight |
| 2002/0123905 A1 | | 9/2002 | Goodroe et al. |
| 2002/0138492 A1 | | 9/2002 | Kil |
| 2002/0138524 A1 | | 9/2002 | Ingle et al. |
| 2002/0143577 A1 | | 10/2002 | Shiffman et al. |
| 2002/0165736 A1 | | 11/2002 | Tolle et al. |
| 2002/0173990 A1 | | 11/2002 | Marasco |
| 2002/0177759 A1 | | 11/2002 | Schoenberg et al. |
| 2003/0046114 A1 | | 3/2003 | Davies et al. |
| 2003/0050794 A1 | | 3/2003 | Keck |
| 2003/0108938 A1 | | 6/2003 | Pickar et al. |
| 2003/0120134 A1 | | 6/2003 | Rao et al. |
| 2003/0120458 A1 | | 6/2003 | Rao et al. |
| 2003/0120514 A1 | | 6/2003 | Rao et al. |
| 2003/0125984 A1 | | 7/2003 | Rao et al. |
| 2003/0125985 A1 | | 7/2003 | Rao et al. |
| 2003/0125988 A1 | | 7/2003 | Rao et al. |
| 2003/0126101 A1 | | 7/2003 | Rao et al. |
| 2003/0130871 A1 | | 7/2003 | Rao et al. |
| 2003/0135391 A1 | * | 7/2003 | Edmundson et al. ........... 705/2 |
| 2003/0208382 A1 | | 11/2003 | Westfall |
| 2004/0078216 A1 | | 4/2004 | Togo |
| 2004/0243586 A1 | * | 12/2004 | Byers ........................ 707/100 |
| 2005/0187794 A1 | | 8/2005 | Kimak |
| 2006/0064415 A1 | | 3/2006 | Guyon et al. |

FOREIGN PATENT DOCUMENTS

| | | |
|---|---|---|
| EP | 0 596 247 A2 | 5/1994 |
| EP | 0 641 863 | 3/1995 |
| EP | 0 917 078 A1 | 10/1997 |
| GB | 2 332 544 A | 6/1999 |
| JP | 11328073 A | 11/1999 |
| JP | 2001297157 A | 10/2001 |
| WO | WO 98/29790 | 7/1998 |
| WO | 98/39720 | 9/1998 |
| WO | WO 00/51054 | 8/2000 |
| WO | WO 00/69331 | 11/2000 |
| WO | WO 01/66007 | 9/2001 |
| WO | WO 01 78005 A | 10/2001 |
| WO | 01/82173 A1 | 11/2001 |

OTHER PUBLICATIONS

Lean Suan Ong et al: "The colorectal Cancer Recurrence Support (CARDS) system" 1997, Elsevier, Netherlands, vol. 11, No. 3, pp. 175-188, XP002270752 ISSN: 0933-3657 abstract figure 1 Section 6.

Kamp V et al: "Database system support for multidimensional data analysis in environmental epidemiology" Database Engineering and Aplications Symposium, 1997. Ideas 97. Proceedings., International Montreal, Que., Canada Aug. 25-27, 1997, Los Alamitos, CA, USA, IEEE Comput. Soc, US, Aug. 25, 1997, pp. 180-188, XP010250142 ISBN: 0-8186-8114-4 p. 180-p. 188.

"Machine Learning and Data Mining", Mitchell, Communications of the ACM, Nov. 1999, ACM, USA, Online!, vol. 42, No. 11, Nov. 1999, pp. 30-36, retrieved from internet: http://portal.acm.org/ft_gateway.cfm?

"Data Mining for the Enterprise", Kleissner, System Sciences, 1998. Proceedings of the Thirty- First Hawaii International Conference on Kohala Coast, HI, USA Jan. 6-9, 1998, Los Alamitos, CA, USA, IEEE Comput. Soc. US, Jan. 6, 1998, pp. 295-304.

"Improved Diagnostic and Prognostic Assessments Using Health Management Information Fusion", Roemer et al., 20001 IEEE Autotestcon Proceedings, IEEE Systems Readiness Technology Conference, Autotestcon 2001, vol. Conf. 37, Aug. 20, 2001, pp. 365-377.

"Data Mining for Disease Management: Adding Value to Patient Records", Rao et al., Electromedia, Online!, vol. 68, 2000, pp. 63-67, retrieved from the internet: http://www.med.siemens.com/medroot/en/news/electro/issues/pdf/onco_2000_e/9.pdf.

"Information Understanding Integrating Data Fusion and Data Mining Processes", Waltz et al, Circuits and Systems, 1998, ISCAS 98, Proceedings of the 1998 IEEE International Symposium on Monterey, CA, USA May 31-Jun. 3, 1998, NY, NY, USA, IEEE, May 31, 1998, pp. 553-556.

"A Mutually Beneficial Integration of Data Mining and Information Extraction", Nahm et al., Proceedings AAAI, National Conference on Artificial Intelligence, Jul. 30, 2000, pp. 627-632.

Grimes, "Structure, Models and Meaning, Is "Unstructured" Data Merely Unmodeled?", Mar. 1, 2005, Intelligent Enterprise, http://www.intelligententerprise.com/show/Article.jhtml?articleID=59301538.

Berkus, "Unstructured Data" as an Oxymoron, Sep. 1, 2005, ITtoolbox Blogs, http://blogs.ittoolbox.com/database/soup/archives/unstructured-data-as-an-oxymoron-5588.

Larsen, "Fast and effective text mining using linear-time document clustering", 1999, ACM Press, Conference on Knowledge Discovery in Data, Proceedings of the fifth ACM SIGKDD International Conference on Knowledge Discovery and Data Mining, pp. 16-22.

Rao, "From Unstructured Data to Actionable Intelligence", IT Pro, Nov./Dec. 2003, pp. 29-35.

Mills, "Computer Technology of the Not-too-distant Future", Sep. 1993, Medical Laboratory Observer, vol. 25, No. 9, p. 78.

Duda, "Pattern Classification", 2001, John Wiley & Sons, Inc., p. vii-xx, Chapter 1.

Hudson. "The feasibility of using automated data to assess guideline-concordant care for schizophrenia", Dec. 4, 1999, Journal of Medical Systems, vol. 23, No. 4, pp. 299-307.

PR Newsire, Diabetes Health Management Award Honors Mayor Clinic's Zimmerman, Sep. 25, 2000.

Hudson, "CAATS and compliance", Apr. 1998, The Internal Auditor, vol. 55, No. 2, p. 25.

Hofer, "The Unreliability of Individual Physician "Report Cards" for Assessing the Costs and Quality of Care of a Chronic Disease", Jun. 9, 1999, JAMA, vol. 281, No. 22:2098-2105.

King et al., MEDUS/A: Distributing Database Management for Medical Research, Proceedings of Computer Networks Compcon 82, Sep. 20-23, 1982, pp. 635-642.

Boxwala et al., "Architecture for a Multipurpose Guideline Execution Engine", Proc. AMIA Symp 1999, pp. 701-705.

Guidance for Institutional Review Boards and Clinical Investigators 1998 Update, Sep. 1998, U.S. Food and Drug Administration.

Kassirer, "The Use and Abuse of Practice Profiles", Mar. 3, 1994, The New England Journal of Medicine, vol. 330:634-636.

Chen, "Do "America's Best Hospitals" Perform Better for Acute Myocardial Infarctions?", Jan. 28, 1999, The New England Journal of Medicine, vol. 340, No. 4:286-292.

* cited by examiner

PATIENT DATA MINING FOR LUNG CANCER SCREENING

CROSS REFERENCE TO RELATED APPLICATIONS

This application claims the benefit of U.S. Provisional Application Ser. No. 60/335,542, filed on Nov. 2, 2001, which is incorporated by reference herein in its entirety.

FIELD OF THE INVENTION

The present invention relates to medical information processing systems, and, more particularly to a computerized system and method for screening patients for lung cancer, monitoring nodule detection in patients and managing patients exhibiting lung cancer indications.

BACKGROUND OF THE INVENTION

In the United States, lung cancer is the second most common cause of cancer and the leading cause of cancer deaths for both men and women. Survival from lung cancer is dependent on the stage of the cancer. The stage is determined by the size and location of nodules (e.g., tumors), the presence of cancer in the surrounding lymph nodes, and the spread of cancer to distant sites. When lung cancer is treated in its earliest stage, the cure rate approaches 70% or greater. Therefore, early detection is crucial for increasing the survival rates for patient with lung cancer.

Traditionally, X-rays have been used to detect nodules in patients showing symptoms of lung cancer. However, the smallest nodule detectable by X-ray is approximately 1 cm, which is an indication of advance growth, and subsequently, survival rates for patients exhibiting these nodules are low. Computerized tomography (CT) scans are capable of detecting lung cancer nodules much smaller than by conventional X-rays. CT scans have a much higher resolution than X-rays and can detect a nodule at only 0.5 mm in diameter.

Although CT scans can detect very small nodules, CT screening is expensive. Determining whether detected nodules are malignant requires multiple CT examinations over several months to make sure that the nodule does not grow. Furthermore, most patients screened have some "junk" in their lungs which may show up as a nodule in a CT scan due to its high resolution. However, every nodule can not be biopsied for several reasons. First, as with multiple CT scans, a biopsy is expensive. Most importantly, a biopsy causes much anxiety in patients due to the fact it is an invasive procedure and it has a certain amount of risk associated with it. Therefore, a protocol for lung cancer screening needs to balance the costs associated with the tests to be performed and the burden placed upon the patients while maintaining a high quality of care.

In view of the above, there exists a need for improved systems and methods for screening persons for lung cancer, monitoring nodule detection, and managing patients exhibiting lung cancer indications.

SUMMARY OF THE INVENTION

According to one aspect of the present invention, a lung cancer screening system is provided including a database including structured patient information for a patient population and a domain knowledge base including information about lung cancer; an individual patient record; and a processor for analyzing the patient record with data from the database to determine if a patient has indications of lung cancer. The database being populated with the structured patient information by data mining structured and unstructured patient records or is populated with information collected prospectively.

In another aspect, the processor further includes a diagnosis module for determining a current state of a patient. The diagnosis module analyzes an imaging study, e.g., a computerized tomography (CT) scan, to detect if a nodule is present and, if a nodule is present, registering the imaging study (CT scan) with previous imaging studies of the patient to determine growth of the nodule.

In a further aspect of the present invention, the processor further includes a modeling module for analyzing the population-based structured patient information of the database to determine trends in patients with similar characteristics of the patient as determined by the individual patient record. The modeling module predicts a progression of lung cancer in the patient based on a determined trend.

In another aspect of the present invention, the processor further comprises a patient management module for determining a screening protocol for the patient. The patient management module determines an optimal time for a next testing procedure. Additionally, the patient management module balances costs of potential tests to be preformed against a risk of late detection of lung cancer to determine a maximum allowable time between tests for the individual patient.

According to yet another aspect of the present invention, a method for screening for lung cancer is provided. The method includes the steps of inputting patient-specific data into a patient record; performing at least one lung cancer screening procedure on a patient, wherein at least one result from the at least one procedure is inputted into the patient record in a structured format; and analyzing the patient record with a domain knowledge base to determine if the patient has indications of lung cancer. The method further includes the step of diagnosing a current state of the patient.

In a further aspect, the method further includes the step of analyzing a database of structured patient information for a patient population to create a model of a similar patient with similar characteristics of the patient based on the patient record; and determining a progression of lung cancer in the patient based on the model. The database of population-based structured patient information is compiled by mining data of population-based patients based on the domain knowledge base, wherein the data is stored in structured and unstructured formats.

In still a further aspect of the present invention, the method includes the step of determining a screening protocol for the patient based on the model. The screening protocol includes an optimal time for a next procedure based on the model.

In another aspect of the present invention, the inputting of patient-specific data into the patient record is performed by mining historical data of the patient, the historical data being in structured and unstructured formats.

In yet another aspect, the performing step includes conducting an imaging study, e.g., a computerized tomography (CT) scan of the patient; and detecting nodules present in the scan. The analyzing step includes registering the CT scan with previous CT scans; and determining growth of the detected nodules over the several scans.

According to a further aspect of the present invention, a program storage device readable by a machine, tangibly embodying a program of instructions executable by the machine to perform method steps for screening for lung cancer is provided including the method steps of inputting patient-specific data into a patient record; performing at least one lung cancer screening procedure on a patient, wherein at least one result from the at least one procedure is inputted into the patient record in a structured format; and analyzing the patient record with a domain knowledge base to determine if the patient has indications of lung cancer.

BRIEF DESCRIPTION OF THE DRAWINGS

The above and other aspects, features and advantages of the present invention will become more apparent from the following detailed description when taken in conjunction with the accompanying drawings in which.

DESCRIPTION OF PREFERRED EMBODIMENTS

To facilitate a clear understanding of the present invention, illustrative examples are provided herein which describe certain aspects of the invention. However, it is to be appreciated that these illustrations are not meant to limit the scope of the invention, and are provided herein to illustrate certain concepts associated with the invention.

It is also to be understood that the present invention may be implemented in various forms of hardware, software, firmware, special purpose processors, or a combination thereof. Preferably, the present invention is implemented in software as a program tangibly embodied on a program storage device. The program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the program (or combination thereof) which is executed via the operating system. In addition, various other peripheral devices may be connected to the computer platform such as an additional data storage device and a printing device.

It is to be understood that, because some of the constituent system components and method steps depicted in the accompanying figures are preferably implemented in software, the actual connections between the system components (or the process steps) may differ depending upon the manner in which the present invention is programmed.

Figure 1:
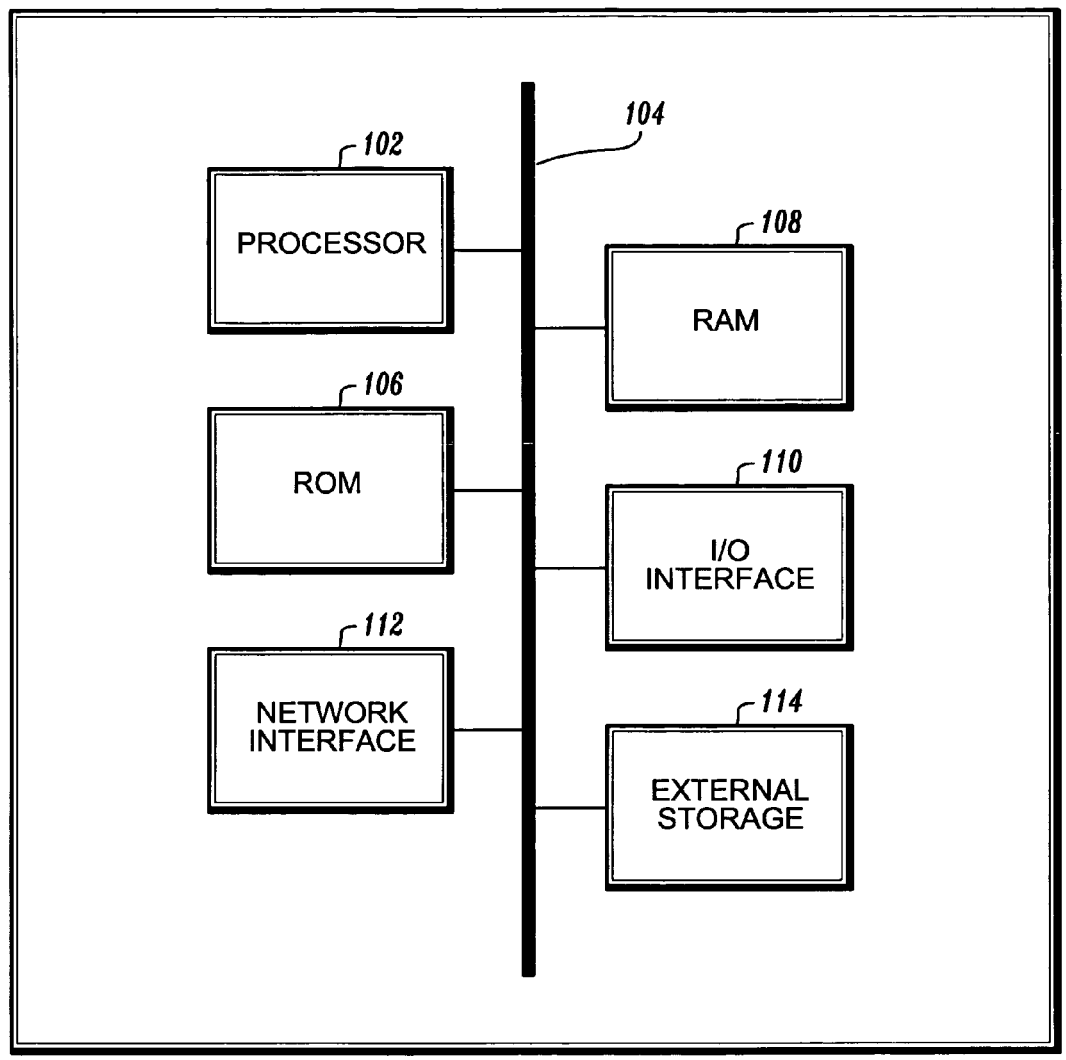
FIG. 1 is a block diagram of a computer processing system to which the present invention may be applied according to an embodiment of the present invention.

FIG. 1 is a block diagram of a computer processing system 100 to which the present invention may be applied according to an embodiment of the present invention. The system 100 includes at least one processor (hereinafter processor) 102 operatively coupled to other components via a system bus 104. A read-only memory (ROM) 106, a random access memory (RAM) 108, an I/O interface 110, a network interface 112, and external storage 114 are operatively coupled to the system bus 104. Various peripheral devices such as, for example, a display device, a disk storage device (e.g., a magnetic or optical disk storage device), a keyboard, and a mouse, may be operatively coupled to the system bus 104 by the I/O interface 110 or the network interface 112.

The computer system 100 may be a standalone system or be linked to a network via the network interface 112. The network interface 112 may be a hard-wired interface. However, in various exemplary embodiments, the network interface 112 can include any device suitable to transmit information to and from another device, such as a universal asynchronous receiver/transmitter (UART), a parallel digital interface, a software interface or any combination of known or later developed software and hardware. The network interface may be linked to various types of networks, including a local area network (LAN), a wide area network (WAN), an intranet, a virtual private network (VPN), and the Internet.

The external storage 114 may be implemented using a database management system (DBMS) managed by the processor 102 and residing on a memory such as a hard disk. However, it should be appreciated that the external storage 114 may be implemented on one or more additional computer systems. For example, the external storage 114 may include a data warehouse system residing on a separate computer system.

Those skilled in the art will appreciate that other alternative computing environments may be used without departing from the spirit and scope of the present invention.

Figure 2:
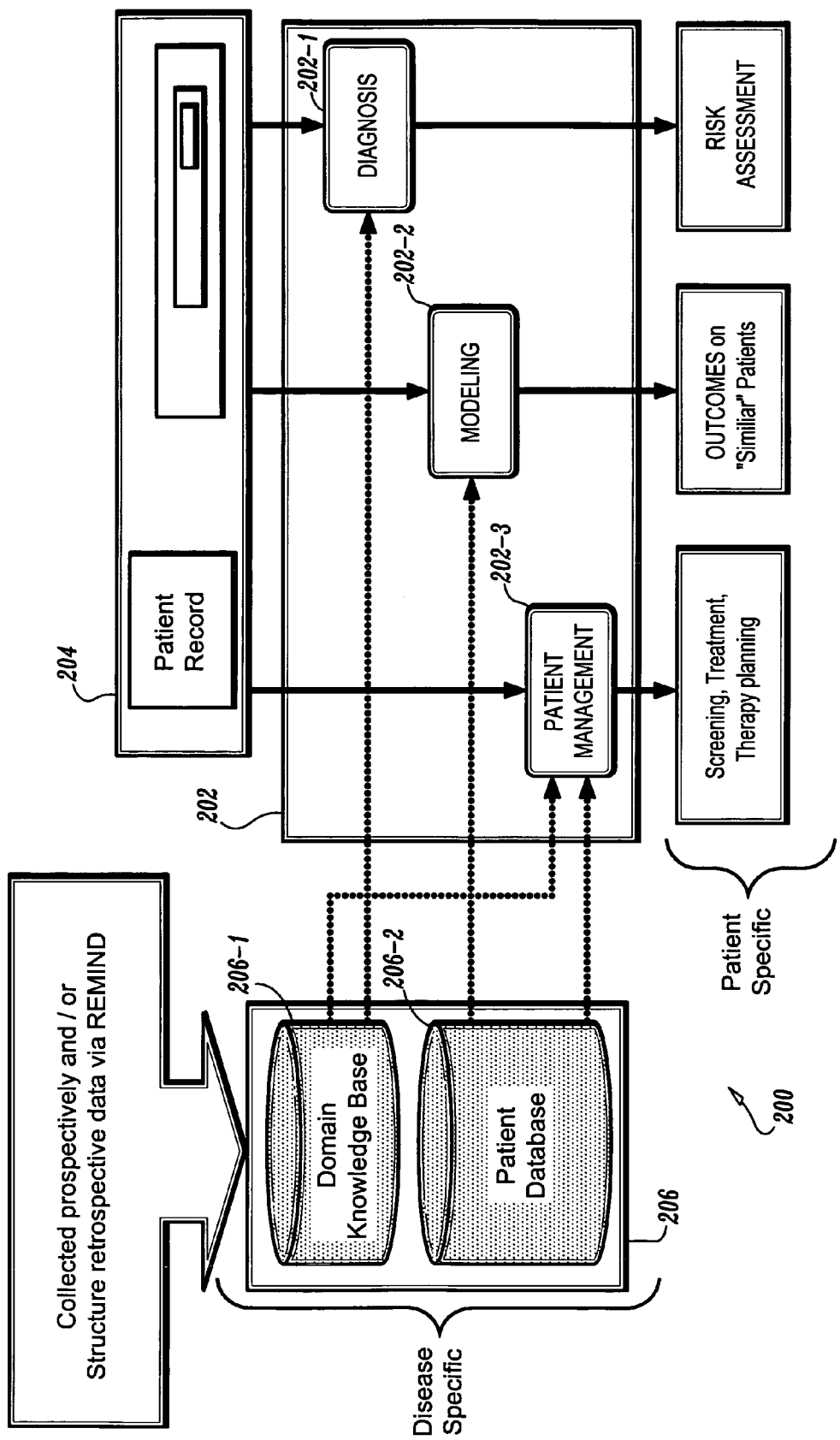
FIG. 2 illustrates an exemplary lung cancer screening system according to an embodiment of the present invention.

Referring to FIG. 2, an exemplary lung cancer screening system 200 according to an embodiment of the present invention is illustrated. The lung cancer screening system 200 includes processor 202 which includes a plurality of modules for performing different tasks. The processor 202 is coupled to a structured database 206 compiled for a disease of interest, here, lung cancer. The processor 202 will interact with the structured database 206 to determine certain outputs relating to a specific patient based on the specific patient's record 204. The patient record 204 may include demographic information, family history, results of initial tests, images from a CT scan, doctors' dictations, etc.

Preferably, the structured database 206 is populated with population-based patient information using data mining techniques described in "Patient Data Mining," by Rao et al., copending U.S. patent application Ser. No. 10/287,055, filed herewith, which is incorporated by reference herein in its entirety. That patent application teaches a data mining framework for mining high-quality structured clinical information. The data mining framework preferably includes a data miner, having functions and capabilities as in the REMIND system, commercially available from Siemens Medical Solutions, that mines medical information from computerized patient records (CPRs) based on domain-specific knowledge contained in a knowledge base. The CPRs may be of structured and/or unstructured formats. The domain-specific knowledge may relate to a disease of interest, a hospital, etc. The data miner includes components for extracting information from the CPRs, combining all available evidence in a principled fashion over time, and drawing inferences from this combination process. The mined medical information is stored in the structured CPR database, such as database 206.

Here, the domain knowledge base 206-1 relates to lung cancer and the patient database 206-2 is a structured database populated with information mined from a plurality of computerized patient records (CPRs) wherein the patients either had lung cancer, exhibited symptoms or indications of lung cancer and/or participate in activities which increase their risk of developing lung cancer, e.g., smoking. Alternatively, the information stored in the patient database 206-2 may be prospectively collected.

The lung cancer screening system 200 interacts with the specific patient record 204 and the structured database 206 to determine the patient present condition, determine the future chances of the patient developing lung cancer and determine suggested future treatment of the patient. Each task performed by the lung cancer screening system 200 is performed by an executable module residing either in the processor of the system 202 and/or in a memory device (e.g., RAM, ROM, external storage, etc.) of the system.

A diagnosis module 202-1 interacts with the patient record 204 and the domain knowledge base 206-1 to determine the current state of the patient, e.g., a diagnosis, and any risk assessment. The diagnosis module 202-1 will combine all available information about the patient and perform a probabilistic inference on patient-specific issues based on the domain knowledge base 206-1, using techniques described in "Patient Data Mining for Diagnosis and Projections of Patient States," by Rao et al., copending U.S. patent application Ser. No. 10/287,053, filed herewith, which is incorporated by reference herein in its entirety. This may entail reviewing an imaging study, e.g., a CT scan, included in the patient record 204 and determining if the CT scan includes a nodule and, if so, determining the size of the nodule.

In one embodiment, the diagnosis module 202-1 may perform volumetric serial studies on several CT scans taken over a period of time. Each CT scan image will be inputted into the screening system and any nodules discovered will be extracted by imaging processes known in the art. Each nodule will be analyzed for shape, size, position and risk. Each successive CT scan will be registered with the previous scan to estimate a growth distribution of the nodules over time. The domain knowledge base 206-1 will then be used to determine, based on the size of the nodule, rate of growth, if the nodule is a cause for concern. For example, if a detected nodule is greater than 1 cm, the diagnosis module may determine there is a 20% probability that the screened patient is in Stage I.

Additionally, the domain knowledge base 206-1 will impose criteria on other aspects of the patient record 204 to determine if there is a cause for concern. For example, the system may increase the probability that the patient is in Stage I if it is determined the patient is a heavy smoker. Alternatively, the system may decrease the probability that the patient is in Stage I if the patient record shows that the detected nodule has been the same size for more than two years.

Similarly, nodule information may be extracted from a radiologist's dictations by a natural language processing module. The diagnosis module 202-1 will use the domain knowledge base to reconcile any conflicts between the image processing and the natural language processing. For example, if the natural language processing has extracted from a doctor's dictation that the patient exhibits no indications of lung cancer but the image processing indicates the patient has several nodules which have doubled in size over the last three months, the system will, based on growth rates in the knowledge base, assign a high probability to Stage I lung cancer.

Additionally, the diagnosis module 202-1 may employ the domain knowledge base 206-1 to establish relationships between test values and demographics to other variables.

A modeling module 202-2 interacts with the patient record 204 and the patient database 206-2 to determine the potential progression of the patient or to determine future chances of the disease occurring. The modeling module 202-2 reviews the patient database 206-2 for records of patients with similar characteristics of the current patient as determined by the patient record 204. For example, if the current patient is a male, age forty who smokes five packs of cigarettes a day, the modeling module will extract only those patient records that are with an acceptable range of the current patient's characteristics. The modeling module 202-2 will conduct a retrospective CPR analysis on the structured database 206 to look for trends of outcomes of these "similar" patients to predict the progression of the lung cancer in the current patient, for example, automatically identify interesting patterns between genetic markers, outcomes, demographics and therapy, for instance, white males, age forty who have been smoking five packs of cigarettes a day for twenty years tend to develop nodules at age 52. All recommendations or prognosis may be shown as statistics on similar patients.

A patient management module 202-3 interacts with the patient record 204, domain knowledge base 206-1 and patient database 206-2 to determine a screening protocol for the patient, e.g., an optimal time for a next procedure and/or an optimal procedure to be next performed. For example, if a detected nodule in a patient has grown 100% in three months, the system will recommend a follow-up CT scan in three months; alternatively, if the nodule exhibits no growth, the system will recommend a follow-up CT scan in twelve months.

Additionally, the patient management module 202-3 will generate a treatment and therapy planning guideline for the patient. When compiling a proposed protocol for the specific patient, the patient management module 202-2 will balance the costs of the potential tests to be performed against a risk of late detection of lung cancer with the model generated above to find a maximum allowable time between tests to ensure quality of care. For example, if a detected nodule has no growth over the last eighteen months, the system may recommend a follow-up visit to be two years later since no growth indicates a lower risk for developing cancer.

Figure 3:
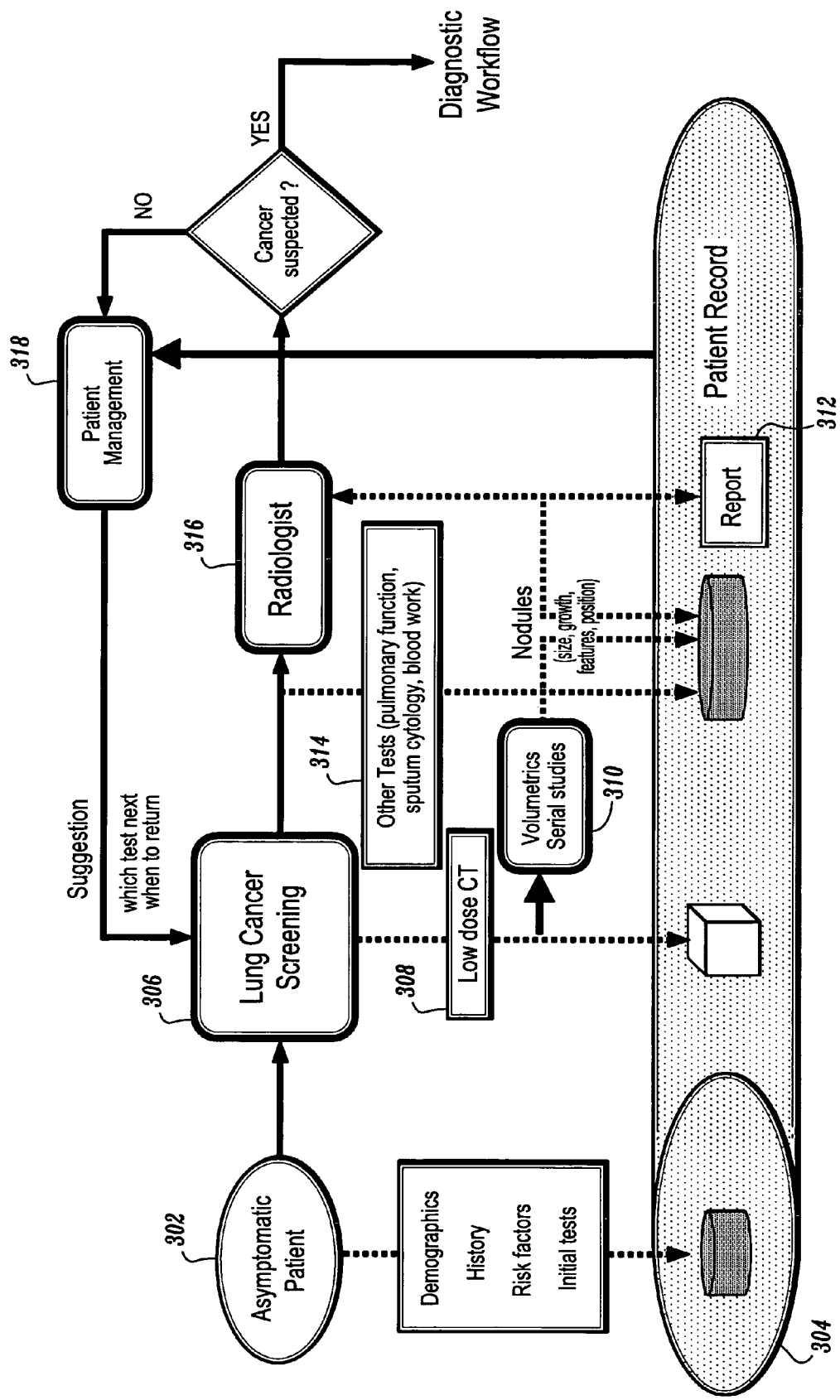
FIG. 3 illustrates a flow diagram for screening, monitoring and managing a patient according to an embodiment of the present invention.

Referring to FIG. 3, a work flow diagram illustrates how the lung cancer screening system can assist an appropriate medical professional in diagnosing, monitoring and managing a patient with lung cancer and/or lung cancer indications.

An asymptomatic patient 302 submits himself to a lung cancer screening procedure 306. Before the procedure takes place, a patient record 304 is created for the patient. It is to be understood that patient record 304 is the same as patient record 204 used in the lung cancer screening system 200 of FIG. 2. The patient record 304 is populated with data from a questionnaire (for example, information such as demographics, family history, smoking history, etc.), results of initial tests, genetic markers, radiologists' clinical findings, etc. Additionally, the patient record may be populated by mining data from the historical records of the patient, as described in the copending application identified above. The lung cancer screening procedure 306 may include any of the following: a physical examination, chest X-ray, CT scan, positron emission tomography (PET) scan, a magnetic resonance imaging (MRI) scan, sputum cytology, bronchoscopy, blood work, pulmonary function tests, etc.

The results of the lung cancer screening procedures are inputted to the system and stored in a structure format in the patient record 304. Before being stored in the patient record, any CT scan 308 performed is processed for nodule detection and management via volumetrics serial studies 310 performed by the diagnosis module 202-1. For an initial CT scan, the scan is analyzed to determine if any nodules of interest are present via the diagnosis module 202-1 of the lung cancer screening system 200. If any nodules are present, their position, size, and/or features are determined and are stored in the patient record. The results from the volumetrics study of the nodules are combined in a report 312 with the results of the other procedures 314 to be presented to the appropriate medical professional 316, for example, a radiologist or oncologist. The report may include a probabilistic determination of the current state of the patient, e.g., there is at least a 20% chance of malignant lung cancer.

Based on the report 312, the appropriate medical professional will make a determination of the current state of the patient. This determination may be made solely on the report generated by the lung cancer screening system. Alternatively, the determination may be made by comparing the results in the report to a model of a similar patient generated by the modeling module 202-2 of the system 200. If cancer is suspected, the patient will be sent for a further diagnostic workflow, for example, a biopsy.

If cancer is not suspected at this time, the medical professional's determinations and any further comments are added to the patient record 304. If any suspicious nodules are detected, the patient record is reviewed for patient management 318 to determine an appropriate screening protocol, i.e., the timing of the next visit, what tests are to be performed next, etc., via the patient management module 202-3 of the lung cancer screening system 200. The screening protocol may be determined for the specific patient by querying the structured database 206 with the patient record 304 to find similar patients and to determine their outcomes in accordance with their proscribed treatments and/or therapies. The screening protocol for the specific patient may entail determining the optimal time for the next CT scan, blood test, etc. and/or identifying all potential lung cancer incidents before an adverse event occurs, e.g., stage II cancer or metastases.

The lung cancer screening system and method of the present invention provides for a rapid review of a large volume data set. The system and method allows all available information to be used in diagnosing, monitoring and managing patients with lung cancer and/or patients exhibiting indications of lung cancer. By accessing all available information of a specific patient and a plurality of patients, the system and method will assess the need for a patient to get diagnostic workup or remain in screening, estimate when the patient should return for follow-up study and project lung cancer risk into the future.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for screening for lung cancer, the method comprising the steps of:
    inputting patient-specific data into a patient record, the patient-specific data representing the patient;
    performing at least one lung cancer screening procedure on a patient, wherein at least one result from the at least one procedure is input into the patient record;
    mining data of the patient record based on a domain knowledge base specific to lung cancer, wherein the data of the patient record is stored in structured and unstructured formats, and wherein the mining comprises populating, with populated data, a structured database compiled for lung cancer from the structured and unstructured data;
    analyzing, with a processor, the populated data of the structured database with the domain knowledge base to determine whether the patient has indications of lung cancer; and
    presenting a report as a function of a result of the analyzing;
    further comprising the steps of:
    analyzing the structured database of structured patient information for a patient population to create a model of a similar patient with similar characteristics of the patient based on the patient record; and
    determining a progression of lung cancer in the patient based on the model, wherein the structured database of population-based structured patient information is compiled by mining data of population-based patients based on the domain knowledge base, wherein the data is stored in structured and unstructured formats.

2. The method as in claim 1, further comprising the step of diagnosing a current state of the patient.

3. The method as in claim 1, further comprising the step of determining a screening protocol for the patient based on the model.

4. The method as in claim 3, wherein the screening protocol includes a time for a next procedure for the individual patient based on the model.

5. The method as in claim 4, wherein the next testing procedure is a computerized tomography (CT) scan.

6. The method as in claim 4, further comprising the step of balancing costs of potential tests to be performed against a risk of late detection of lung cancer to determine a maximum allowable time between tests for the individual patient.

7. The method as in claim 3, further comprising the steps of determining a testing procedure to be next performed for the individual patient and determining a time for the testing procedure for the individual patient.

8. The method as in claim 1, wherein the performing step includes
    conducting an imaging study of the patient; and
    detecting nodules present in the imaging study.

9. The method as in claim 8, wherein the analyzing step includes
    registering the imaging study with previous imaging studies; and
    determining growth of the detected nodules over the imaging studies.

10. The method as in claim 8, wherein the imaging study is a computerized tomography (CT) scan.

11. The method as in claim 1 wherein the patient-specific data in the patient record includes information other than derived from an image, and wherein the analyzing comprises analyzing at least the information other than derived from an image with the domain knowledge base.

12. The method as in claim 1 wherein analyzing comprises making a probabilistic inference from information in the patient record as a function of the domain knowledge base.

13. The method of claim 1 wherein mining comprises combining evidence and inferring from the combination.

14. The method of claim 1 wherein analyzing the structured database comprises resolving conflicts based on the domain knowledge base.

15. A method for screening for lung cancer, the method comprising the steps of:
    inputting patient-specific data into a patient record, the patient-specific data representing the patient;
    performing at least one lung cancer screening procedure on a patient, wherein at least one result from the at least one procedure is input into the patient record;
    analyzing, with a processor, the patient record with a domain knowledge base to determine whether the patient has indications of lung cancer;
    wherein the inputting of patient-specific data into the patient record is performed by mining historical data of the patient, the historical data being in structured and unstructured formats, the mining based on the domain knowledge base specific to lung cancer, wherein the mining comprises populating a structured database compiled for lung cancer from the structured and unstructured data, and wherein the analyzing of the patient record comprises analyzing from the structured database compiled for lung cancer; and presenting a report as a function of a result of the analyzing; further comprising the steps of:

analyzing the structured database of structured patient information for a patient population to create a model of a similar patient with similar characteristics of the patient based on the patient record; and determining a progression of lung cancer in the patient based on the model, wherein the structured database of population-based structured patient information is compiled by mining data of population-based patients based on the domain knowledge base, wherein the data is stored in structured and unstructured formats.

16. A program storage device readable by a machine, tangibly embodying a program of instructions executable by the machine to perform method steps for screening for lung cancer, the method steps comprising:

inputting patient-specific data into a patient record, the patient-specific data representing the patient;

performing at least one lung cancer screening procedure on a patient, wherein at least one result from the at least one procedure is input into the patient record;

mining data for the patient record based on a domain knowledge base specific to lung cancer, wherein the data of the patient record is stored in structured and unstructured formats, and wherein the mining comprises populating a structured database compiled for lung cancer from the structured and unstructured data;

analyzing, with the machine, the patient record of the structured database with the domain knowledge base to determine whether the patient has indications of lung cancer; and presenting a report as a function of a result of the analyzing; further comprising the steps of:

analyzing the structured database of structured patient information for a patient population to create a model of a similar patient with similar characteristics of the patient based on the patient record; and determining a progression of lung cancer in the patient based on the model, wherein the structured database of population-based structured patient information is compiled by mining data of population-based patients based on the domain knowledge base, wherein the data is stored in structured and unstructured formats.

17. The storage device as in claim 16 wherein the patient-specific data in the patient record includes information other than derived from an image, and wherein the analyzing comprises analyzing at least the information other than derived from an image with the domain knowledge base.

18. The storage device as in claim 16 wherein analyzing comprises making a probabilistic inference from information in the patient record as a function of the domain knowledge base.

19. A program storage device readable by a machine, tangibly embodying a program of instructions executable by the machine to perform method steps for screening for lung cancer, the method steps comprising:

inputting patient-specific data for a patient into a patient record, the patient-specific data representing the patient;

determining position, size, features, or combinations thereof of nodules shown in an image from a scan of the patient;

inputting the position, size, feature, or combination thereof into the patient record;

mining first data from the patient record and based on a domain knowledge base specific to lung cancer, wherein the patient record is stored in structured and unstructured formats, and wherein the mining comprises mining from the structured and unstructured data of the patient record, the first data including information mined from demographic, family history, test result, doctor's notes, and the position, size, features, or combinations thereof information from the structured and unstructured data;

analyzing, by the machine, the first data with the domain knowledge base to determine whether the patient has indications of lung cancer; and presenting a report as a function of a result of the analyzing; further comprising the steps of:

analyzing the structured database of structured patient information for a patient population to create a model of a similar patient with similar characteristics of the patient based on the patient record; and determining a progression of lung cancer in the patient based on the model, wherein the structured database of population-based structured patient information is compiled by mining data of population-based patients based on the domain knowledge base, wherein the data is stored in structured and unstructured formats.

* * * * *